United States Patent
Fujiwara et al.

(10) Patent No.: US 11,583,619 B2
(45) Date of Patent: Feb. 21, 2023

(54) METHOD FOR REGENERATING ADSORBER AND DIALYSIS SYSTEM

(71) Applicant: Nikkiso Co., Ltd., Tokyo (JP)

(72) Inventors: Masato Fujiwara, Makinohara (JP); Hiroshi Nimura, Makinohara (JP); Takayoshi Yokoyama, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 142 days.

(21) Appl. No.: 16/768,008

(22) PCT Filed: Nov. 27, 2018

(86) PCT No.: PCT/JP2018/043600
§ 371 (c)(1),
(2) Date: May 28, 2020

(87) PCT Pub. No.: WO2019/107357
PCT Pub. Date: Jun. 6, 2019

(65) Prior Publication Data
US 2020/0360588 A1 Nov. 19, 2020

(30) Foreign Application Priority Data
Nov. 29, 2017 (JP) .............................. JP2017-228862

(51) Int. Cl.
*A61M 1/16* (2006.01)
*A61M 1/36* (2006.01)

(52) U.S. Cl.
CPC .......... *A61M 1/1696* (2013.01); *A61M 1/169* (2013.01); *A61M 1/1688* (2014.02); *A61M 1/3655* (2013.01); *A61M 2202/0498* (2013.01)

(58) Field of Classification Search
CPC .. A61M 1/1682; A61M 1/1688; A61M 1/169; A61M 1/1696; A61M 1/3655; A61M 2202/0498
See application file for complete search history.

(56) References Cited

U.S. PATENT DOCUMENTS 3,909,377 A 9/1975 Bizot et al.
4,118,314 A * 10/1978 Yoshida .............. A61M 1/1696
210/140
(Continued)

FOREIGN PATENT DOCUMENTS

DE 19917522 A1 10/2000
JP S5234154 B 9/1977
(Continued)

OTHER PUBLICATIONS

Extended European Search Report issued in EP18882395.9 dated Apr. 19, 2021.
Office Action issued in JP2019557237 dated Sep. 20, 2022.

*Primary Examiner* — Dirk R Bass
(74) *Attorney, Agent, or Firm* — The Webb Law Firm (57) ABSTRACT

A method for regenerating an adsorber which has a porous body and does not have an enzyme includes a dialysis step, in which the adsorber is connected to a dialysate circulation unit to cause uremic substances within a dialysate to be adsorbed onto the adsorber, and a regenerating step, in which the uremic substances which are adsorbed on the adsorber are desorbed by regenerating water that flows in a regenerating water flow unit. A dialysis system is equipped with the dialysate circulation unit, the adsorber, which is connected to the dialysate circulation unit, and the regenerating water flow unit. The regenerating water flow unit is connectable to the adsorber.

10 Claims, 3 Drawing Sheets

(56) References Cited

U.S. PATENT DOCUMENTS

| | | | |
|---|---|---|---|
| 4,857,181 A | 8/1989 | Shouldice et al. |
| 6,132,627 A | 10/2000 | Joko et al. |
| 2017/0143887 A1 | 5/2017 | Cho |

FOREIGN PATENT DOCUMENTS

| | | |
|---|---|---|
| JP | S63192450 A | 8/1988 |
| JP | S649029 B2 | 2/1989 |
| JP | H245318 A | 9/1993 |
| JP | H724064 A | 1/1995 |
| JP | 10174976 A | 6/1998 |
| JP | 2003251338 A | 9/2003 |

* cited by examiner

METHOD FOR REGENERATING ADSORBER AND DIALYSIS SYSTEM

CROSS-REFERENCE TO RELATED APPLICATIONS

This application is the United States national phase of International Application No. PCT/JP2018/043600 filed Nov. 27, 2018, and claims priority to Japanese Patent Application No. 2017-228862 filed Nov. 29, 2017, the disclosures of which are hereby incorporated by reference in their entirety.

BACKGROUND OF THE INVENTION

Field of the Invention

The present disclosure is related to a method for regenerating an adsorber and a dialysis system.

Description of Related Art

Conventionally, there is a method for removing harmful substances from a blood filtrate in an ultrafiltration type blood purification apparatus.

The method for removing harmful substances employs two or more adsorbers which are filled with nitrogen containing fibrous activated carbon adsorbent alternately or in a predetermined order to adsorb harmful substances with one or more adsorbers. Harmful substances are desorbed (regeneration of the adsorber) from the one or more adsorbers which have adsorbed the harmful substances and are not currently being utilized for adsorption. That is, adsorption of the harmful substances by the adsorbers and desorption of the harmful substances from the adsorbers are alternately conducted during treatment in which a patient's blood is circulated through an ultrafiltration membrane refer to Japanese Examined Application Publication No. S64-9029.

The method for removing harmful substances from adsorbers in a conventional conventional blood purification apparatus requires a large and complex apparatus, and it is difficult to change the installation location of such a blood purification apparatus.

SUMMARY OF THE INVENTION

According to one aspect of the present disclosure, a method for regenerating an adsorber, which has a porous body and does not have an enzyme, is provided. The method for regenerating an adsorber includes:

a dialysis step in which the adsorber is connected to a dialysate circulation unit to adsorb uremic substances in a dialysate onto the adsorber; and a regenerating step following the dialysis step, in which the uremic substances which are adsorbed onto the adsorber are removed by regenerating water that flows in a regenerating water flow unit.

According to the present disclosure, it is possible to provide a method for regenerating an adsorber and a dialysis system that facilitates changing installation locations of a blood purification apparatus.

DESCRIPTION OF THE INVENTION

Hereinafter, embodiments will be described in detail with reference to the attached drawings.

Hereinafter, a first aspect (hereinafter, referred to as "first embodiment") will be described in detail with reference to the drawings. Note that the same elements will be denoted by the same reference numbers or reference symbols throughout the entirety of the description of the embodiments. Note that in the following description, unless otherwise specified, the term "treatment" refers to a state in which the blood of a patient 200 is being circulated through a dialyzer 30 in a blood circulation unit 10, and the term "regeneration" refers to a state in which the blood of the patient 200 is not being circulated in the blood circulation unit 10. Note that although the present embodiment shows an example applied to hemodialysis, the present disclosure is not limited to such a configuration. The present disclosure may be applied to all blood purification treatments such as hemofiltration and hemofiltration dialysis. Note that in the following description, the term "dialysis" refers to dialysis treatment.

Figure 1A:
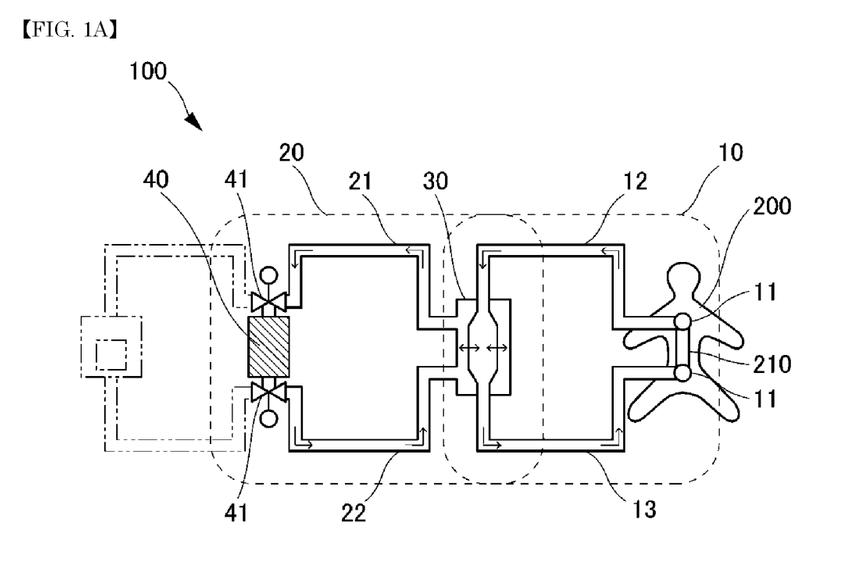
FIG. 1A is a diagram for explaining a dialysis system according to a first embodiment during treatment.
Figure 1B:
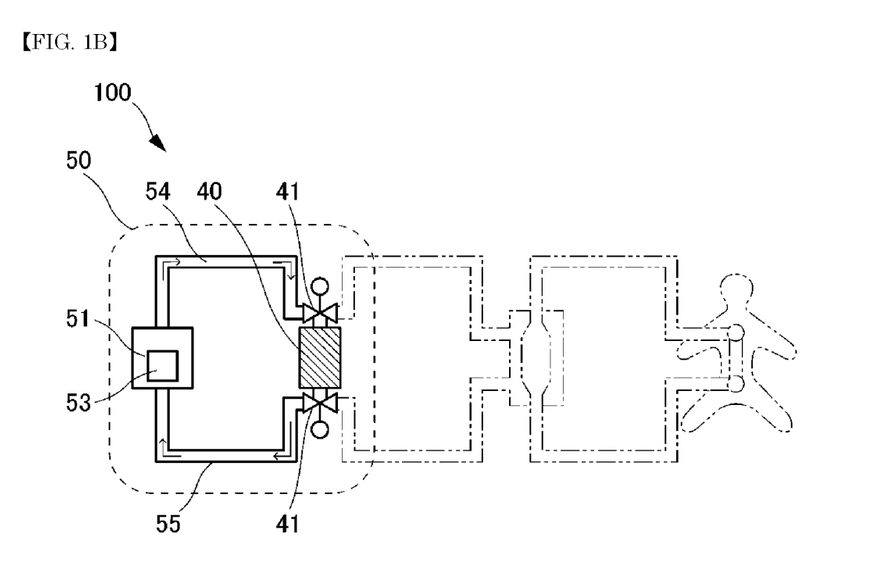
FIG. 1B is a diagram for explaining the dialysis system according to the first embodiment during regeneration.

FIG. 1A is a diagram for explaining a dialysis system 100 according to a first embodiment during treatment, and FIG. 1B is a diagram for explaining the dialysis system 100 according to the first embodiment during regeneration.

Dialysis System

The dialysis system 100 according to the first embodiment is a blood purification apparatus for performing hemodialysis treatment. The dialysis system 100 performs hemodialysis by guiding the blood of the patient 200 to the dialyzer 30, which is external of the patient's body, and returning purified blood to the body of the patient 200.

In greater detail, the dialysis system 100 is equipped with a dialysate circulation unit 20 which is connected to the blood circulation unit 10 via the dialyzer 30, an adsorber 40 (adsorption column) having a porous body, and a regenerating water flow unit 50, as illustrated in FIG. 1A and FIG. 1B.

The blood circulation unit 10 is a component for circulating blood between a shunt 210 which is applied to the body of the patient 200 and the dialyzer 30 which is provided external of the body of the patient 200. The blood circulation unit 10 includes an arterial blood circuit 12 and a venous blood circuit 13 that connect the dialyzer 30 to the shunt 210 via a first connection unit 11. In addition, functional units such as a blood pump, a supplemental fluid supply line, an anticoagulant injection unit, an air trap chamber, a measuring instrument, and a monitoring device, which are not illustrated, are provided in the blood circulation unit 10 as appropriate.

The dialyzer 30 is an artificial kidney that purifies the blood of the patient 200 by exchanging substances between the blood of the patient 200 and a dialysate through the operations of diffusion and filtration through a semipermeable membrane. The dialyzer 30 is, for example, that in which a plurality of fine tubes formed by a semipermeable membrane, through which the blood of the patient 200 passes, are covered with a cylindrical body through which the dialysate passes, as a component of the dialysate circulation unit 20.

The dialysate circulation unit 20 is a component for circulating the dialysate between the dialyzer 30 and the adsorber 40. The dialysate circulation section 20 includes dialysate circuits 21 and 22 that connect the adsorber 40 to the dialyzer 30 via a third connection (not illustrated). In addition, functional units such as a dialysate pump, a dialysate supply line, a balance chamber, a heater, a drainage line, a measuring device, a monitoring device, and a dialysate control apparatus, which are not illustrated, are provided in the dialysate circulation unit 20 as appropriate.

The adsorber 40 includes a porous body which is capable of directly adsorbing uremic substances. That is, the adsorber 40 is an adsorber that can directly adsorb uremic substances. Accordingly, in the present embodiment, it is not practically necessary for the adsorber 40 to have an enzyme for decomposing urea, such as urease. Accordingly, in the present specification, the "adsorber 40 not having an enzyme" means that the adsorber 40 is practically free of an enzyme for decomposing urea. The expression "practically free of an enzyme for decomposing urea" means that an aspect that contains an enzyme for decomposing urea in an amount that does not practically function (for example, if an amount of urea which is adsorbed by the porous body is designated as X [g] and the amount of urea decomposed by an enzyme is designated as Y [g], the aspect is that in which $Y/(X+Y) \leq 0.1$) is not excluded. Note that in the following, it is assumed that the adsorber 40 does not contain any enzymes, including an enzyme for decomposing urea or an enzyme for another use, but may contain a small amount of an enzyme for another use.

In addition, the adsorber 40 may include a layer of the porous body which is capable of directly adsorbing uremic substances and layers of other elements. In this case, the layers of the other elements may contain enzymes. In this case, the "adsorber not having an enzyme" refers to the portion of the porous body layer which is capable of directly adsorbing the uremic substances in the adsorber 40.

A carbon based adsorbent is an example of the porous body which is capable of directly adsorbing a uremic substance. The carbon based adsorbent may be, for example, an aggregate of natural products having a porous structure such as activated carbon particles, or an aggregate of formed products having a porous structure such as beads that have pores with an average pore diameter of about 8 nm. As described above, because the adsorber 40 has the carbon based adsorbent, the adsorbed uremic substance can be easily desorbed (removed) with regenerating water. Accordingly, it is possible for the adsorber 40 to be regenerated. Here, the uremic substances include urea, creatinine, potassium, etc.

Here, the regenerating water is water that practically does not contain urea. Examples of the regenerating water include: a liquid in which urea which is contained in utilized regenerating water has been electrolyzed; RO water; physiological saline; unused dialysate, or tap water. Tap water is utilized after being disinfected as appropriate. Note that with respect to the regenerating water that contains urea which is desorbed from the adsorber 40, the urea is removed by electrolysis as will be described later. However, there are cases in which it is difficult to completely remove urea at this time. Therefore, there are cases in which the liquid, obtained by electrolyzing urea which is contained in the utilized regenerating water, contains urea at a certain concentration. In addition, basically, the lower the concentration of urea contained in the regenerating water, the higher the regeneration ability (the ability to desorb urea from the adsorber 40) will become.

In addition, the adsorber 40 does not have an enzyme for decomposing urea. Therefore, it is not necessary to add or exchange enzymes in order to regenerate the activity of the enzymes that decreases accompanying the decomposition of urea over time. Therefore, the adsorber 40 can be maintained in a fixed state in the dialysate circulation unit 20, and the dialysis system 100, that is, the blood purification apparatus, can be made compact.

The regenerating water flow unit 50 is a flow channel for causing regenerating water to flow from a regenerating water control apparatus 51 to the adsorber 40. Note that the first embodiment will be described as an example of a flow channel in which the regenerating water flow unit 50 circulates regenerating water by causing regenerating water to flow from the regenerating water control apparatus 51 to the adsorber 40 and returning the regenerating water to the regenerating water control apparatus 51. Alternatively, the regenerating water flow unit 50 may be a flow channel that causes fresh regenerating water, which is supplied by waterworks, etc., to the adsorber 40 and then discharges the regenerating water without circulating it, to discard the regenerating water. That is, the regenerating water flow unit 50 may be a flow channel that causes regenerating water to flow to the adsorber 40 without passing through the regenerating water control apparatus 51 and additionally without circulating the regenerating water.

The regenerating water control apparatus 51 is connected to respective connection switching units 41 at the upstream side of the adsorber 40 (the side at which the dialysate containing the uremic substance flows into the adsorber 40) and the downstream side (the side at which the dialysate from which uremic substances are desorbed flows out from the adsorber 40) via regenerating water circuits 54 and 55. Note that the regenerating water circuits 54 and 55 may be equipped with second connection units 52 (not illustrated in FIG. 1; refer to FIG. 2B) which are capable of being connected to the respective connection switching units 41 on the upstream side and the downstream side of the adsorber 40. In addition, the regenerating water flow unit 50 is provided with functional units such as a regenerating water supply line, a regenerating water pump, and a drain line, as appropriate.

In addition, the regenerating water flow unit 50 is equipped with an electrolytic tank 53 for electrolyzing desorbed urea, that is, urea which is contained in the utilized regenerating water that flows in the regenerating water flow unit 50. Specifically, the electrolytic tank 53 stores a portion of the regenerating water that circulates in the regenerating water flow unit 50 and causes DC current to flow to a portion of the stored regenerating water in order to electrolyze urea, which is dissolved in the regenerating water by being desorbed from the adsorber 40 and is a urotoxin. Note that the electrolytic tank 53 includes a gas discharge unit for discharging gas which is generated by electrolysis.

Thereby, the adsorbed urea, which is a urotoxin, can be effectively dissolved, so that the amount of regenerating water, which is generally about 18 liters, can be reduced approximately 1 liter, for example. In addition, the amount of regenerating water which is generally utilized is approximately 18 liters as a result of calculating the amount which is required when the regenerating water is caused to flow at a flow rate of 50 mL/min for 6 hours. In the case of the embodiment that includes the electrolytic tank 53, it is only necessary for a priming volume (filling amount) of the adsorber 40 and the other components to be satisfied. Therefore, it is possible to reduce the volume of the required amount of regenerating water to approximately 1 liter.

Here, as shown in the change from the state illustrated in FIG. 1A to the state illustrated in FIG. 1B, the regenerating water flow unit 50 is connectable to the adsorber 40. Specifically, for example, the adsorber 40 is equipped with the connection switching units 41 that have the function of switching valves that switch the connection between the regenerating water flow unit 50 and the dialysate circulation unit 20 on the upstream side and the downstream side of the dialysate circulation unit 20, respectively.

The connection switching units 41 cut off the connection with the regenerating water flow unit 50 when connected to the dialysate circulation unit 20, and cut off the connection with the dialysate circulation unit 20 when connected to the regenerating water flow unit 50.

Note that the regenerating water flow unit 50 may be connectable to the connection switching unit 41 of the adsorber 40 by the second connection unit 52 which is provided in the regenerating water circuits 54 and 55. Thereby, the adsorber 40 can be disconnected from the dialysate circuits 21 and 22 of the dialysate circulation unit 20 and connected to the regenerating water circuits 54 and 55 of the regenerating water flow section 50 between a dialysis step and a regeneration step.

Because the regenerating water flow unit 50 is connectable to the adsorber 40 in this manner, it is possible for the regenerating water flow unit 50 that includes the regenerating water control apparatus 51 to be separated from the dialysate circulation unit 20. Therefore, as illustrated in FIG. 1A, during treatment, a space for installing the regenerating water flow unit 50 that includes the regenerating water control apparatus 51 adjacent to the dialysate circulation unit 20 is unnecessary, and it is only necessary to secure a space for installing each of the functional units which are provided in the blood circulation unit 10 and the dialysate circulation unit 20. Accordingly, the dialysis system 100, that is, the blood purification device can be made compact and can be easily installed in different locations.

Method for Regenerating Adsorber

Next, a method for regenerating the adsorber 40 that employs the dialysis system 100 of the first embodiment will be described.

The method for regenerating the adsorber 40 according to the present embodiment can be applied to the regeneration of the adsorber 40 having the porous body.

(1) First, as illustrated in FIG. 1A, the first connection unit 11 of the blood circulation unit 10 is connected to the shunt 210 of the patient 200, and the adsorber 40 having the porous body is connected to the dialysate circulation unit 20. Uremic substances which are present in a dialysate is adsorbed to the adsorber 40 (dialysis step). The first connection unit 11 is a component for connecting the arterial blood circuit 12 and the venous blood circuit 13 of the blood circulation unit 10 to the shunt 210 of the patient 200, and directly pierces the shunt 210 of the patient 200. The first connection unit 11 is equipped with a piercing needle (not shown), and a shunt connector (not shown) for detachably connecting the piercing needle to the arterial blood circuit 12 and the venous blood circuit 13.

Specifically, the connection between the adsorber 40 and the regenerating water flow unit 50 is switched and connected to the dialysate circulation section 20 by the connection switching section 41, and a dialysate control apparatus (not shown) is driven. By this dialysis step, the uremic substances which are present in the blood of the patient 200 are adsorbed onto the adsorber 40, and the blood of the patient 200 is purified.

(2) Next, as illustrated in FIG. 1B, the circulation unit to which the adsorber 40 is connected is switched from the dialysate circulation unit 20 to the regenerating water flow unit 50 by the connection switching unit 41. Note that the adsorber 40 may be separated from the dialysate circulation unit 20, and then the connection switching unit 41 of the adsorber 40 may be switched to a connection with the regenerating water flow unit 50 thereafter.

(3) Then, after the dialysis step, the regenerating water control apparatus 51 is driven, and the uremic substances which are adsorbed on the adsorber 40 are desorbed by the regenerating water that flows through the regenerating water flow unit 50 (regenerating step).

This regenerating step desorbs the uremic substances which are adsorbed on the adsorber.

(4) The regenerating water that flows through the regenerating water flow unit 50 during the regeneration step is electrolyzed.

(5) Subsequently, after the regeneration step, the adsorber 40 and the regenerating water flow unit 50 that includes the regenerating water circuits 54 and 55 is cleansed and/or disinfected by heating, etc. (cleansing/disinfecting step). As an alternative to disinfection by heating, disinfection by a chemical solution (sodium hypochlorite, peracetic acid, etc.) may be conducted.

In the cleansing/disinfecting step, the adsorber 40 and the regenerating water flow unit 50 that includes the regenerating water circuits 54 and 55 may be independently cleansed and/or disinfected. Thereby, the regenerating water flow unit 50 can be reused.

Further, the dialysate circulation unit 20 that includes the dialysate circuits 21 and 22 may be cleansed and/or disinfected in the cleansing/disinfecting step in addition to the regenerating water flow unit 50. Thereby, the regenerating water stream 50 and the dialysate circulation unit 20 can be reused.

Still further, the dialysate circulation unit 20 and the blood circulation unit 10 that includes the dialyzer 30, the arterial blood circuit 12, and the venous blood circuit 13 may be cleansed and/or disinfected in the cleansing/disinfecting step in addition to the regenerating water flow unit 50. Thereby, the regenerating water flow unit 50, the dialysate circulation unit 20, and the blood circulation unit 10 can be reused.

(6) The adsorber 40 is connected to the dialysate circulation unit 20 to execute the dialysis step again.

(7) The dialysis step and the regeneration step are alternately repeated.

By performing the regeneration step after performing the dialysis step in this manner, the uremic substances which are adsorbed on the adsorber 40 can be desorbed and the adsorber 40 can be regenerated. Therefore, it is not necessary to separate the desorber 40 from the dialysate circulation unit 20, the configuration of the dialysis system 100 need not be complex, and the operation for regenerating the adsorber 40 is simplified. Further, because the adsorber 40 can be regenerated a plurality of times by repeating the dialysis step and the regenerating step, it is not necessary to separate the desorber 40 from the dialysate circulation unit 20, the configuration of the dialysis system 100 need not be complex, and the operation for regenerating the adsorber 40 is simplified.

Note that because there is a cleansing/disinfecting step between the regeneration step and the next dialysis step, not only RO water but also ordinary water such as non-disinfected tap water may be utilized as the regenerating water. Because tap water supplied from waterworks may be utilized, there are advantages that transport is not required as in the case that water stored in a physiological saline solution bag is utilized, and an RO water manufacturing apparatus is not required as in the case that RO water is utilized. It is only necessary to connect the dialysis system 100 to waterworks, which is simple.

Figure 2A:
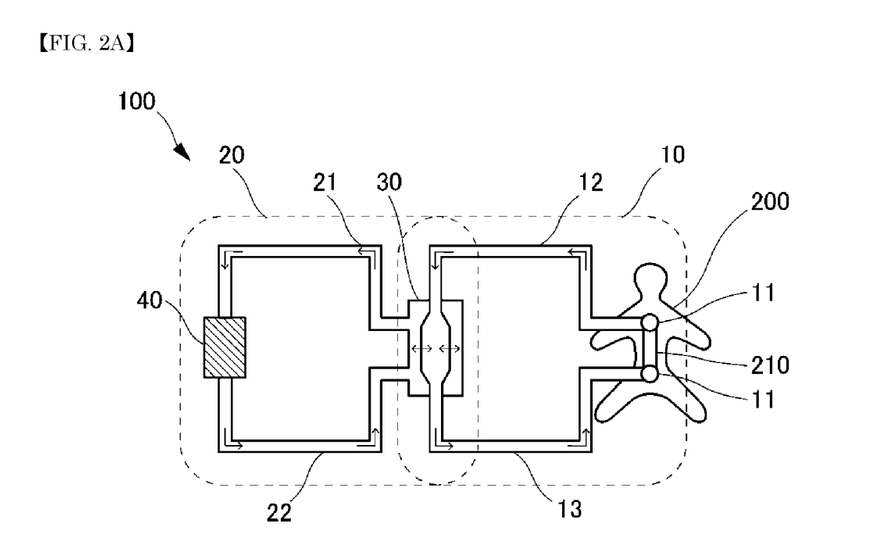
FIG. 2A is a diagram for explaining a dialysis system according to a second embodiment during treatment.
Figure 2B:
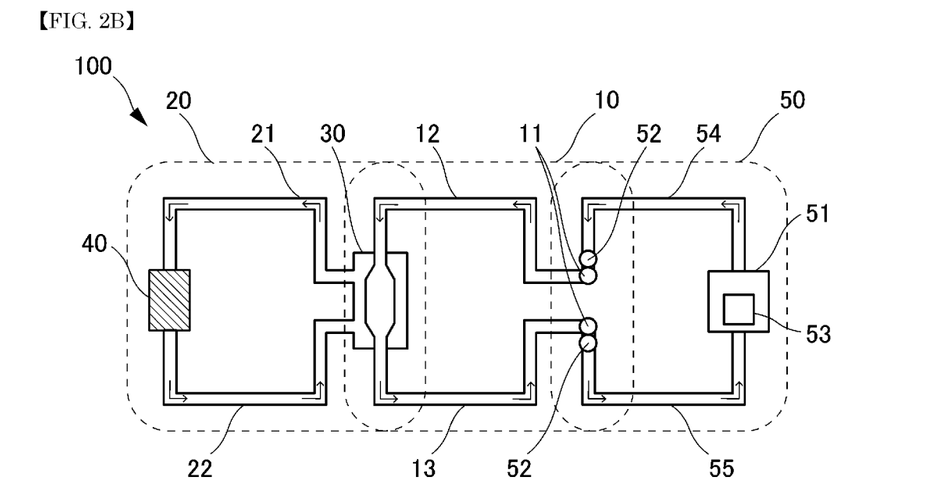
FIG. 2B is a diagram for explaining the dialysis system according to the second embodiment during regeneration.

Next, a second aspect (hereinafter, referred to as "second embodiment") will be described in detail with reference to the drawings. The second embodiment differs from the first embodiment mainly in the point that the regenerating water flow unit 50 is connectable to the first connection unit 11. In addition, the regeneration method during regeneration differs between the second embodiment and the first embodiment. Descriptions of points which are the same as those of the first embodiment may be omitted.

FIG. 2A is a diagram for explaining a dialysis system 100 according to the second embodiment during treatment, and FIG. 2B is a diagram for explaining the dialysis system 100 according to the second embodiment during regeneration.

Dialysis System

Similarly to the dialysis system 100 of the first embodiment, the dialysis system 100 of the second embodiment is equipped with a dialysate circulation unit 20 which is connected to a blood circulation unit 10 via a dialyzer 30, an adsorber 40 (adsorption column) having a porous body, and a regenerating water flow unit 50, as illustrated in FIG. 2A and FIG. 2B.

However, more specifically, the regenerating water flow unit 50 is connectable to the first connection unit 11, which is for connecting blood circuits 12 and 13 of a blood circulation unit 10 to a shunt 210, as shown in the change from the state which is illustrated in FIG. 2A to the state which is illustrated in FIG. 2B. Thereby, the regenerating water flow unit 50 is indirectly connectable to the adsorber 40 through the blood circulation unit 10 that includes the first connection unit 10, and a dialysate circulation unit 20. In addition, the regenerating water flow unit 50 is also indirectly connectable to the adsorber 40 by utilizing the first connection unit 11 for connecting to the shunt 210. Therefore, the adsorber 40 does not require a special structure, such as a connection switching unit 41 for switching between a connection with the regenerating water flow unit 50 and a connection with the dialysate circulation unit 20. Accordingly, the configuration of the adsorber 40 can be simplified.

Method for Regenerating Adsorber

Next, a method for regenerating the adsorber 40 that employs the dialysis system 100 of the second embodiment will be described.

The method for regenerating the adsorber 40 according to the present embodiment can be applied to the regeneration of the adsorber 40 having the porous body.

(1) First, as illustrated in FIG. 2A, the first connection unit 11 of the blood circulation unit 10 is connected to the shunt 210 of the patient 200, and the adsorber 40 having the porous body is connected to the dialysate circulation unit 20. Uremic substances which are present in a dialysate is adsorbed to the adsorber 40 (dialysis step). in a manner similar to the method for regenerating the adsorber 40 that employs the dialysis system 100 of the first embodiment.

Specifically, a dialysate control apparatus (not shown), which is provided in the dialysate circulation unit 20 to which the adsorber 40 is connected, is driven. By this dialysis step, the uremic substances which are present in the blood of the patient 200 are adsorbed onto the adsorber 40, and the blood of the patient 200 is purified.

(2) Next, following the dialysis step, the adsorber 40 in the dialysate circulation unit 20 is indirectly connected to the regenerating water flow unit 50 via the blood circulation unit 10. That is, the connection of the first connection unit 11 for connecting with the shunt 210 is switched to a connection with the regenerating water flow unit 50.

Specifically, the first connection unit 11 of the blood circulation unit 10 is removed from the shunt 210 of the patient 200 and connected with a second connection unit 52 of the regenerating water flow unit 50. Thereby, the adsorber 40 is indirectly connected to the regenerating water flow unit 50 via the dialysate circulation unit 20 and the blood circulation unit 10.

Here, in greater detail, blood during treatment flows in order from the shunt 210, the arterial piercing needle, the arterial blood circuit 12, the dialyzer 30, the venous blood circuit 13, the venous piercing needle, and to the shunt 210. The shunt 210 and the arterial piercing needle, a shunt connector between the arterial piercing needle and the arterial blood circuit 12, the arterial blood circuit 12 and the dialyzer 30, the dialyzer 30 and the venous blood circuit 13, the shunt connector between the venous blood circuit 13 and the venous piercing needle, and the shunt connector between the venous piercing needle and the shunt 210 are attachable and detachable. For this reason, for example, the arterial blood circuit 12 may be detached from the arterial piercing needle, the venous blood circuit 13 may be detached from the venous piercing needle, the arterial blood circuit 12 and the venous blood circuit 13 may be connected to the piercing needles, and the blood circulation unit. 10 may be connected to the second connection unit 52 of the regenerating water flow part 50 via a shunt connector which is provided between the piercing needles and the blood circulation unit 10. In addition, for example, the arterial piercing needle and the venous piercing needle may be withdrawn from the shunt 210, and the arterial piercing needle and the venous piercing needle may be directly connected to the second connection unit 52 of the regenerating water flow unit 50.

(3) Next, following the dialysis step, a regenerating water control apparatus 51 is driven, and uremic substances which are adsorbed on the adsorber 40 are desorbed by regenerating water that flows through the regenerating water flow unit 50 (regeneration step).

(4) The regenerating water that flows through the regenerating water flow unit 50 during the regeneration step is electrolyzed.

(5) Subsequently, after the regeneration step, the dialysate circulation unit 20 that includes the adsorber 40, the blood circulation unit 10, and the regenerating water flow unit 50 are cleansed and/or disinfected by heating, etc. (cleansing/disinfecting step). Note that as an alternative to disinfection by heating, disinfection by a chemical solution (sodium hypochlorite, peracetic acid, etc.) may be conducted. Thereby, the regenerating water flow unit 50, the dialysate circulation unit 20, and the blood circulating nit 10 can be reused.

(6) The adsorber 40 is connected to the shunt 210 of the patient 200 via the dialysate circulation unit 20 and the first connection unit 11 of the blood circulation unit 10 to execute the dialysis step again.

(7) The dialysis step and the regeneration step are alternately repeated.

The method for regenerating the adsorber 40 according to the second embodiment utilizes the first connection unit 11 of the blood circulation unit 10 in the manner described above, and therefore, compared to the method for regenerating the adsorber 40 according to the first embodiment, the method for regenerating the adsorber 40 according to the second embodiment is more effective than that of the first embodiment, because there is no switching step for switching the connection by the connection switching unit 41 of the adsorber 40 between the connection with the regenerating water flow unit 50 and the connection with the dialysate circulation unit 20. Therefore, the connection switching unit 41 is not necessary in the adsorber 40, and the operations involved in regeneration of the adsorber 40 can be simplified, and the configuration of the dialysis system 100 can be simplified.

Further, after the dialysis step is performed, by performing the regeneration step, the uremic substance adsorbed on the adsorber 40 can be desorbed and the adsorber 40 can be regenerated. There is no need to disconnect, the dialysis system 100 can be simplified, and the operation for regenerating the adsorber 40 is simplified. Further, because the adsorber 40 can be regenerated a plurality of times by repeating the dialysis step and the regenerating step, there is no need to separate the adsorber 40 from the dialysate circulation unit 20, the dialysis system 100 can be simplified, and the operation for regenerating the adsorber 40 is simplified.

According to the method for regenerating the adsorber 40, the adsorber 40 which has a porous body and does not have an enzyme is regenerated. The dialysis step in which the adsorber 40 is connected to the dialysate circulation unit 20 to adsorb uremic substances onto the adsorber 40 and, after the dialysis step, the regeneration step in which the uremic substances which are adsorbed on the adsorber 40 are desorbed by the regenerating water that flows through the regenerating water flow unit 50 are repeated. The regenerating water flow unit 50 can be spatially separated during treatment. Compared particularly to a dialysis system that presumes that desorption of uremic substances from the adsorber 40 (regeneration of the adsorber 40) is performed simultaneously during treatment, the dialysis system 100 can be made compact during treatment. In addition, the blood purification apparatus which is constituted by the dialysate circulation unit 20 and the blood circulation unit 10, excluding the regenerating water flow unit 50, can be easily installed in different locations.

According to the dialysis system 100, the dialysis system 100 is equipped with the dialysate circulation unit 20 and the adsorber 40 that is connected to the dialysate circulation unit 20 and has a porous body and does not have an enzyme. Because the regenerating water flow unit 50 is connectable to the adsorber 40, the regenerating water flow unit 50 can be spatially separated during treatment. The dialysis system 100 during treatment can be made more compact compared to a dialysis system that presumes that desorption of the uremic substances (regeneration of the adsorber 40) is performed simultaneously with treatment. The blood purification apparatus that includes the dialysate circulation unit 20 and the blood circulation unit 10, excluding the regenerating water flow unit 50, can be made compact, and the blood purification device can be easily installed in different locations.

Next, an embodiment, in which the dialysis system 100 of the first embodiment described above is not changed, but the method for regenerating the adsorber of the first embodiment is changed, will be described as a third embodiment.

The method for regenerating the adsorber 40 according to the present embodiment can be applied to the regeneration of the adsorber 40 having a porous body. The regeneration method of the adsorber 40 according to the present embodiment is different from the method for regenerating the adsorber described as the first embodiment in that the cleaning/disinfecting step after the regeneration step can be omitted or simplified. Hereinafter, the method for regenerating the adsorber 40 according to the present embodiment will be described in detail with reference to FIG. 1A and FIG. 1B again.

(1) First, in a manner similar to the method for regenerating the adsorber 40 that employs the dialysis system 100 of the first embodiment described above, the first connection unit 11 of the blood circulation unit 10 is connected to the shunt 210 of the patient 200. The adsorber 40 having a porous body is connected to the dialysate circulation unit 20 to adsorb uremic substances in the dialysate onto the adsorber 40 (dialysis step), as illustrated in FIG. 1A.

(2) Next, in a manner similar to the method for regenerating the adsorber 40 that employs the dialysis system 100 of the first embodiment, the circulation unit to which the adsorber 40 is connected is switched to the regenerating water flow unit 50 from the dialysate circulation unit 20 by the connection switching unit 41, as illustrated in FIG. 1B. Note that the adsorber 40 may be separated from the dialysate circulation unit 20, and then the connection switching unit 41 of the adsorber 40 may switch to the connection with the regenerating water flow unit 50 thereafter.

(3) Then, after the dialysis step, the regenerating water control apparatus 51 is driven to desorb the uremic substances which are adsorbed on the adsorber 40 by the regenerating water that flows through the regenerating water flow unit 50 (regeneration step). At this time, in the present embodiment, water that contains chloride ions is utilized as the regenerating water. The concentration of chloride ions is adapted to ensure a necessary amount of the amount of hypochlorous acid to be described later, and may be, for example, equal to the concentration of chloride ions in physiological saline. Therefore, physiological saline may be utilized as the regenerating water.

This regeneration step desorbs the uremic substance which are adsorbed on the adsorber 40.

(4) The regenerating water that flows in the regenerating water flow section 50 during the regeneration step is electrolyzed in the electrolytic tank 53. At this time, chloride ions which are contained in the regenerating water are oxidized by electrodes to generate hypochlorous acid. That is, when the regenerating water is electrolyzed, urea is electrolyzed and hypochlorous acid is generated.

In the present embodiment, hypochlorous acid is generated during the regeneration step in this manner. Hypochlorous acid, as is widely known, is capable of being decomposed in aqueous solutions and can be utilized as a disinfectant. Therefore, in the present embodiment, the hypochlorous acid in the regenerating water can function as a disinfectant. Specifically, during the regeneration step as well, because the regenerating water that contains the hypochlorous acid flows through the regenerating water flow unit 50, the regenerating water flow unit 50 can be disinfected.

(5) Subsequently, after the regeneration step, the adsorber 40 and the regenerating water flow unit 50 that includes the regenerating water circuits 54 and 55 is cleansed and/or disinfected by heating, etc. (cleansing/disinfecting step). Note that as an alternative to disinfection by heating, disinfection by a chemical solution (sodium hypochlorite, peracetic acid, etc.) may be conducted.

In the cleansing/disinfecting step, the adsorber 40 and the regenerating water flow unit 50 that includes the regenerating water circuits 54 and 55 may be independently cleansed and/or disinfected. Thereby, the regenerating water flow unit 50 can be reused.

However, in the present embodiment, during the regeneration step, the regenerating water flow unit 50 can be disinfected by utilizing hypochlorous acid which is generated as a byproduct when urea is electrolyzed, as described above. Therefore, it is possible to omit or simplify the cleansing/disinfecting step after the regenerating step described in (5).

Note that in the present embodiment as well, the dialysate circulation unit 20 that includes the dialysate circuits 21 and 22 may be cleansed and/or disinfected in the cleansing/disinfecting step in addition to the regenerating water flow unit 50. Thereby, the regenerating water stream 50 and the dialysate circulation unit 20 can be reused.

Further, the dialysate circulation unit 20 and the blood circulation unit 10 that includes the dialyzer 30, the arterial blood circuit 12, and the venous blood circuit 13 may be cleansed and/or disinfected in the cleansing/disinfecting step in addition to the regenerating water flow unit 50. Thereby, the regenerating water flow unit 50, the dialysate circulation unit 20, and the blood circulation unit 10 can be reused.

(6) The adsorber 40 is connected to the dialysate circulation unit 20 to execute the dialysis step again.

(7) The dialysis step and the regeneration step are alternately repeated.

In this manner, the same effects as those of the first embodiment described above can be obtained by the third embodiment. Further, according to the third embodiment, by utilizing water that contains chloride ions as the regenerating water, it is possible to generate hypochlorous acid as a byproduct during the regeneration step when urea is electrolyzed. In addition, because the regenerating water flow unit 50 can be disinfected utilizing the hypochlorous acid, it is possible to omit or simplify the cleansing/disinfecting step after the regenerating step (in particular, the cleansing/disinfecting step related to the regenerating water flow unit 50).

Next, an embodiment, in which the dialysis system 100 of the second embodiment described above is not changed, but the method for regenerating the adsorber of the second embodiment is changed, will be described as a fourth embodiment.

The method for regenerating the adsorber 40 according to the present embodiment can be applied to the regeneration of the adsorber 40 having a porous body. The regeneration method of the adsorber 40 according to the present embodiment is different from the method for regenerating the adsorber described as the second embodiment in that the cleaning/disinfecting step after the regeneration step can be omitted or simplified. Hereinafter, the method for regenerating the adsorber 40 according to the present embodiment will be described in detail with reference to FIG. 2A and FIG. 2B again.

(1) First, in a manner similar to the method for regenerating the adsorber 40 that employs the dialysis system 100 of the second embodiment described above, the first connection unit 11 of the blood circulation unit 10 is connected to the shunt 210 of the patient 200. The adsorber 40 having a porous body is connected to the dialysate circulation unit 20 to adsorb uremic substances in the dialysate onto the adsorber 40 (dialysis step), as illustrated in FIG. 2A.

(2) Next, in a manner similar to the method for regenerating the adsorber 40 that employs the dialysis system 100 of the second embodiment, the adsorber 40 in the dialysate circulation unit 20 is indirectly connected to the regenerating water flow unit 50 via the blood circulation unit 10, as illustrated in FIG. 2B. That is, the first connection unit 11 for connecting with the shunt 210 is switched from a connection with the shunt 210 to a connection with the regenerating water flow unit 50.

(3) Then, after the dialysis step, the regenerating water control apparatus 51 is driven to desorb the uremic substances which are adsorbed on the adsorber 40 by the regenerating water that flows through the regenerating water flow unit 50 (regeneration step). At this time, in the present embodiment, water that contains chloride ions is utilized as the regenerating water. The concentration of chloride ions is adapted to ensure a necessary amount of the amount of hypochlorous acid to be described later, and may be, for example, equal to the concentration of chloride ions in physiological saline. Therefore, physiological saline may be utilized as the regenerating water.

This regeneration step desorbs the uremic substances which are adsorbed on the adsorber 40.

(4) The regenerating water that flows in the regenerating water flow section 50 during the regeneration step is electrolyzed in the electrolytic tank 53. At this time, chloride ions which are contained in the regenerating water are oxidized by electrodes to generate hypochlorous acid. With regard to this point, it is the same as the case of the third embodiment described above.

In the present embodiment, hypochlorous acid is generated during the regeneration step in this manner. Hypochlorous acid, as is widely known, is capable of being decomposed in aqueous solutions and can be utilized as a disinfectant. Therefore, in the present embodiment, the hypochlorous acid in the regenerating water can function as a disinfectant. Specifically, during the regeneration step as well, because the regenerating water that contains the hypochlorous acid flows through the regenerating water flow unit 50, the regenerating water flow unit 50 can be disinfected.

Here, in the present embodiment, the blood circulation unit 10 is connected to the regenerating water flow unit 50 as illustrated in FIG. 2B. Therefore, the arterial blood circuit 12 and the venous blood circuit 13 within the blood circulation unit 10 can be disinfected by the hypochlorous acid which is contained in the regenerating water in addition to the regenerating water circuits 54 and 55 within the regenerating water flow unit 50. In addition, the dialyzer 30 which is connected to the blood circulation unit 10 can also be disinfected. Further, the regenerating water that reaches the dialyzer 30 via the blood circulation unit 10 can further flow to the dialysate circulation unit 20 via the dialyzer 30. Accordingly, in the present embodiment, the dialysate circuit 21, etc. within the dialysate circulation unit 20 can be disinfected by the hypochlorous acid which is contained in the regenerating water.

(5) Subsequently, after the regeneration step, the dialysate circulation unit 20 that includes adsorber 40, the blood circulation unit 10, and the regenerating water flow unit 50 are cleansed and/or disinfected by heating, etc. (cleansing/disinfecting step). Note that as an alternative to disinfection by heating, disinfection by a chemical solution (sodium hypochlorite, peracetic acid, etc.) may be conducted. Thereby, the regenerating water flow unit 50, the dialysate circulation unit 20, and the blood circulation unit 10 can be reused.

However, in the present embodiment, during the regeneration step, the dialysate circulation unit 20, the blood circulation unit 10, and the regenerating water flow unit 50 can be disinfected by utilizing hypochlorous acid which is generated as a byproduct when urea is electrolyzed, as described above. Therefore, it is possible to omit or simplify the cleansing/disinfecting step after the regenerating step described in (5).

(6) The adsorber 40 is connected to shunt 210 of the patient 200 via the dialysate circulation unit 20 and the blood circulation unit 10 to execute the dialysis step again.

(7) The dialysis step and the regeneration step are alternately repeated.

In this manner, the same effects as those of the second embodiment described above can be obtained by the fourth embodiment. In addition, according to the fourth embodiment, by utilizing water that contains chloride ions as the regenerating water, it is possible to generate hypochlorous acid as a byproduct during the regeneration step when urea is electrolyzed. Because the dialysate circulation unit 20, the blood circulation unit 10, and the regenerating water flow unit 50 can be disinfected by utilizing the hypochlorous acid, it is possible to omit or greatly simplify the cleansing/disinfecting step after the regenerating step.

Next, the results of a test of electrolyzing urea will be described with reference to FIG. 3.

Figure 3:
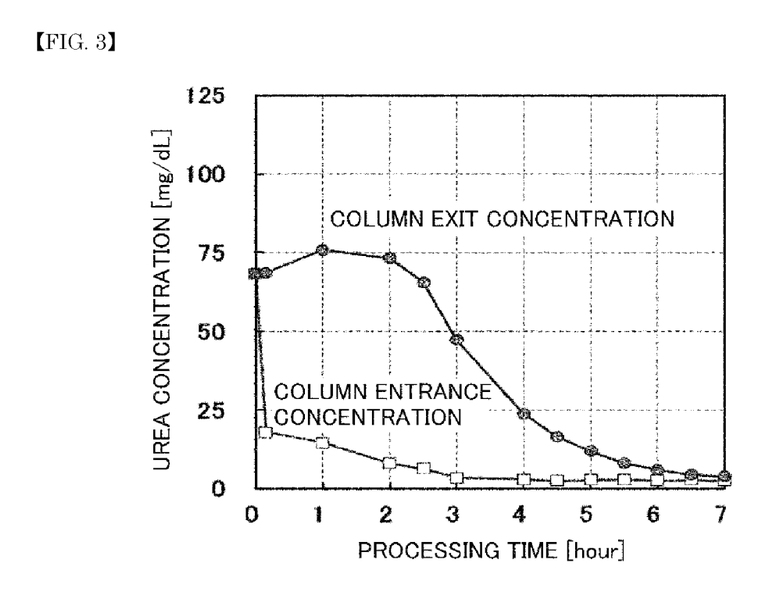
FIG. 3 is a graph that shows the results of a urea electrolysis test.

FIG. 3 is a graph that shows the results of a urea electrolysis test. In FIG. 3, the horizontal axis represents processing time, and the vertical axis represents the concentration of urea. Temporal change properties in a column entrance concentration and temporal change properties in a column exit concentration are indicated.

The test conditions were as follows.

(1) A stock solution as the regenerating water described above was a physiological saline solution (a 0.9% sodium chloride aqueous solution), and the amount was 1 liter.

(2) A column as a porous body of the adsorber 40 was a columnar shape having a diameter of 120 mm and a height of 210 mm, and filled with 2300 ml of an adsorbent. In addition, the column had urea, etc. adsorbed thereon in advance by a simulated treatment (urea concentration of 75 mg/dL). The direction of flow of the stock solution with respect to the column was from bottom to top.

(3) Regarding the electrolytic tank 53, the material of both an anode and a cathode was platinum coated titanium. The electrode area was 662 $cm^2$ for the anode and 607 $cm^2$ for the cathode, and the applied voltage was 5 V direct current.

(4) A tube pump was used as a regenerating water pump, and the flow rate was 50 mL/min.

(5) The stock solution as the regenerating water passed through the column, was subjected to electrolysis in the electrolytic tank 53, and was utilized again in a circulation system to pass through the column again.

In FIG. 3, the column entrance concentration is the concentration of urea in the regenerating water immediately prior to passing through the column, and the column exit concentration is the concentration of urea in the regenerating water immediately following passing through the column.

As shown in FIG. 3, the column entrance concentration decreases rapidly after processing is initiated. From this, it can be understood that electrolysis of urea is being efficiently realized. Note that the initial value of the column entrance concentration (the value when processing is initiated) is the same as the initial value of the column exit concentration (the value when processing is initiated), and is a concentration that substantially corresponds to the concentration of urea which is employed in the simulated treatment (75 mg/dL). From this, it can be understood that desorption of urea from the column is initiated immediately by the regenerating water.

From FIG. 3, it can be understood that the column exit concentration decreases as the processing progresses (as the processing time increases). From this, it can be understood that the urea which is adsorbed on the column decreases accompanying desorption of urea from the column by the regenerating water passing through the column. When the urea which is adsorbed on the column is substantially eliminated, the column exit concentration becomes approximately zero, and the column entrance concentration also becomes approximately zero. In this case, if the processing time becomes approximately seven hours, the column exit concentration and the column entrance concentration become approximately zero, and a state in which continued processing will not practically contribute to regeneration of the column is reached.

Here, the difference between the temporal change properties of the column entrance concentration and the temporal change properties of the column exit concentration corresponds to the concentration of urea which is removed from the column. Accordingly, the temporally integrated value of the difference between these two curves correlates to the total amount of urea removed from the column. From the results shown in FIG. 3, when the total amount of urea removed from the column was calculated, it almost coincided with the total amount of urea which was adsorbed on the column. Therefore, substantially all of the urea which was adsorbed on the column was removed, and it was confirmed that the column was regenerated. That is, the effectiveness of the embodiment described above was confirmed.

Embodiments were described in detail above. However, the present disclosure is not limited to any specific embodiments, and various change and modifications are possible within the scopes which are recited in the claims. In addition, it is also possible to entirely or partially combine the constituent elements of the embodiments which are described above.

The invention claimed is:

1. A method for regenerating an adsorber, which has a porous body and does not have an enzyme, performed in a dialysis system that includes the adsorber and a dialysate circulation unit, the method comprising:
   a dialysis step in which the adsorber is connected to the dialysate circulation unit to adsorb uremic substances in a dialysate onto the adsorber;
   after the dialysis step is completed, installing a regenerating water flow unit to the dialysis system, and connecting the regenerating water flow unit to the adsorber; and
   a regenerating step of removing the uremic substances which are adsorbed on the adsorber by regenerating water that flows in the regenerating water flow unit.

2. The method for regenerating an adsorber as defined in claim 1, further comprising:
   a cleansing/disinfecting step, in which the regenerating water flow unit is cleansed and/or disinfected.

3. The method for regenerating an adsorber as defined in claim 2, wherein:

the cleansing/disinfecting step cleanses and/or disinfects a dialysate circuit and a dialyzer in the dialysate circulation unit.

4. The method for regenerating an adsorber as defined in claim 2, wherein:
the cleansing/disinfecting step cleanses and/or disinfects a blood circuit in a blood circulation unit.

5. The method for regenerating an adsorber as defined in claim 1, wherein:
the regenerating step electrolyzes urea which is contained in the regenerating water that flows in the regenerating water flow unit.

6. The method for regenerating an adsorber as defined in claim 5, wherein:
the regenerating step comprises causing water that contains chloride ions to flow in the regenerating water flow unit as the regenerating water; and
hypochlorous acid is generated during electrolysis of the urea.

7. The method for regenerating an adsorber as defined in claim 1, wherein:
a circulation unit to which the adsorber is connected is switched from the dialysate circulation unit to the regenerating water flow unit after the dialysis step is completed and before the regenerating step.

8. The method for regenerating an adsorber as defined in claim 1, wherein:
the adsorber is separated from the dialysate circulation unit and connected to the regenerating water flow unit after the dialysis step is completed and before the regenerating step.

9. The method for regenerating an adsorber as defined in claim 1, further comprising:
after the dialysis step is completed, disconnecting a first connection unit of a blood circulation unit from a shunt, the first connection provided for connecting a blood circuit of the blood circulation unit to the shunt,
wherein, in the installing and connecting, connecting the regenerating water flow unit to the first connection unit to provide the regenerating water to the adsorber through the first connection unit, the blood circulation unit, and the dialysate circulation unit before the regenerating step.

10. The method for regenerating an adsorber as defined in claim 1, wherein:
the regenerating water flow unit includes a connection unit configured to be connected to and detached from the adsorber.

* * * * *